United States Patent [19]
Coulter et al.

[11] Patent Number: 5,653,686
[45] Date of Patent: Aug. 5, 1997

[54] CLOSED VIAL TRANSFER METHOD AND SYSTEM

[75] Inventors: Wallace H. Coulter, Miami Springs; Charles R. Shambaugh, Coral Gables, both of Fla.

[73] Assignee: Coulter Corporation, Miami, Fla.

[21] Appl. No.: 372,196

[22] Filed: Jan. 13, 1995

[51] Int. Cl.⁶ ..................................... A61M 31/00
[52] U.S. Cl. ........................ 604/56; 604/87; 604/403; 604/411; 604/412; 604/414; 604/415; 604/416
[58] Field of Search ........................... 604/403, 405, 604/411–416, 905, 87–88, 56

[56] References Cited

U.S. PATENT DOCUMENTS

| | | | |
|---|---|---|---|
| 1,526,595 | 2/1925 | Gillman | 604/413 |
| 2,594,621 | 4/1952 | Derrick . | |
| 2,973,758 | 3/1961 | Murrish | 604/413 |
| 3,706,305 | 12/1972 | Berger et al. . | |
| 3,941,171 | 3/1976 | Ogle | 604/413 |
| 3,988,429 | 10/1976 | Richards et al. . | |
| 4,161,857 | 7/1979 | Fraser . | |
| 4,326,541 | 4/1982 | Eckels . | |
| 4,622,222 | 11/1986 | Horvath et al. . | |
| 4,666,850 | 5/1987 | Mehl et al. . | |
| 4,684,365 | 8/1987 | Reinicke | 604/413 |
| 4,697,622 | 10/1987 | Swift et al. | 604/414 |
| 4,740,468 | 4/1988 | Weng et al. . | |
| 5,001,230 | 3/1991 | Brown et al. . | |
| 5,091,304 | 2/1992 | LaDuca et al. . | |
| 5,151,184 | 9/1992 | Ferkany . | |
| 5,163,582 | 11/1992 | Godolphin et al. . | |
| 5,344,036 | 9/1994 | Stanescu et al. | 215/251 |
| 5,352,413 | 10/1994 | Kratzer et al. . | |
| 5,403,304 | 4/1995 | Ishida . | |

OTHER PUBLICATIONS

Hawley's Condensed Chemical Dictionary, 12th Edition, Van Nostrand Reinhold Co., NY, 1993, p. 528.
Catalog—Aldrich Chemical Co., Inc. 1992, pp. 1503–1506
Catalog VMR Scientific, Inc., Scientific Apparatus Catalog 80, 1980, p. 1182

*Primary Examiner*—John G. Weiss
*Assistant Examiner*—P. Zuttarelli
*Attorney, Agent, or Firm*—Mitchell E. Alter

[57] ABSTRACT

A method and transfer device for transferring fluids between closed vials. The transfer device includes a cylinder having a pair of opposing open tubes or tubular portions into which a pair of vials can be inserted to transfer fluid therebetween. The tubes are separated by a wall through which extends a fluid transfer needle and a vent needle which first is inserted into a first vial to vent the first vial into a vent chamber or reservoir formed in the transfer device before the transfer needle is inserted into the first vial. The first vial, stopper first, is inserted into first tube until seated onto an exposed end of the transfer needle. A second vial, stopper first, then is inserted into the second tube until seated onto the opposite exposed end of the transfer needle. A pressure differential between the closed vials preferably can be utilized to transfer a desired fluid portion between the vials.

32 Claims, 2 Drawing Sheets

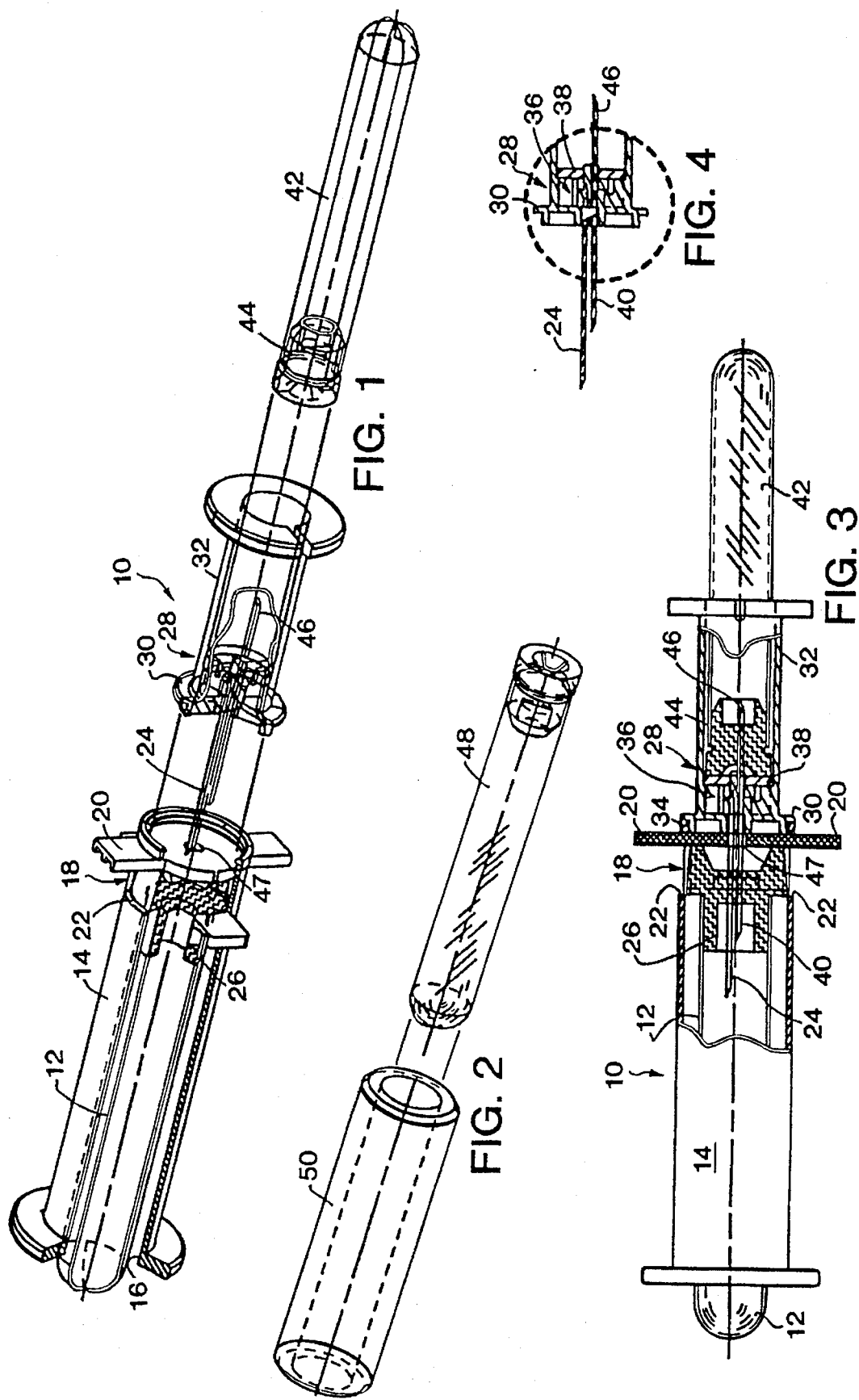

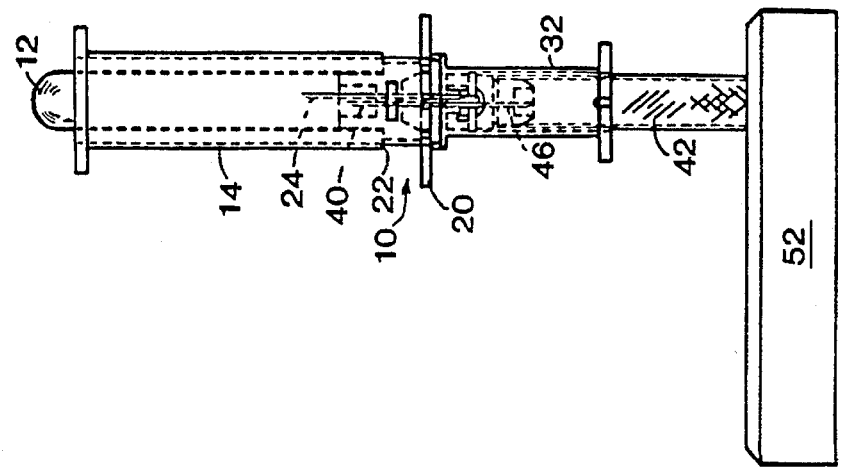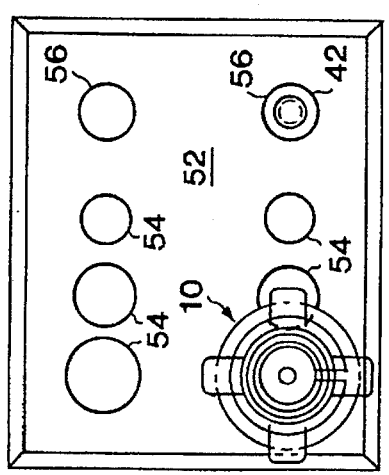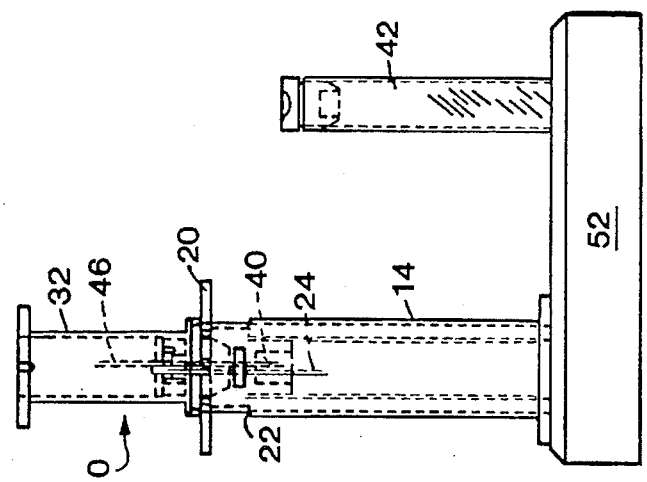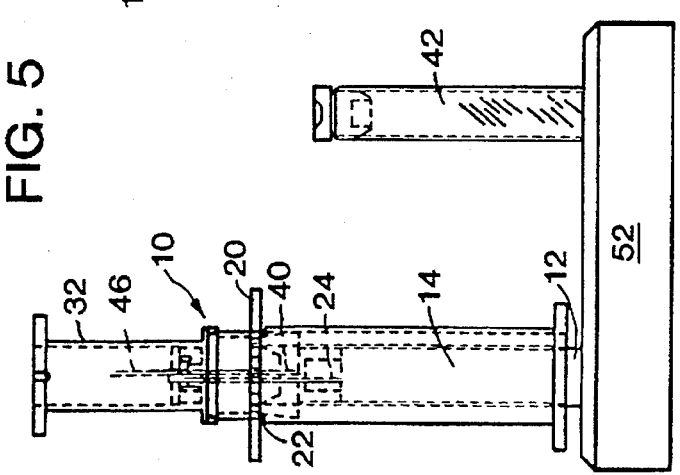
FIG. 5
FIG. 6
FIG. 7
FIG. 8

5,653,686

CLOSED VIAL TRANSFER METHOD AND SYSTEM

BACKGROUND OF THE INVENTION

This invention relates generally to transferring a fluid from one vial to another. More particularly, the invention is directed to transferring an aliquot of a fluid, such as blood, from one closed vial to another without exposing an operator to the fluid.

Automated blood and blood cell analyzers are well known. These analyzers typically utilize a portion of a whole or pre-prepared blood sample. When the blood sample is taken from a subject, it usually is placed into a vial or test tube. With the potential of exposure to highly infectious diseases by an operator, such as the HIV virus or hepatitis, the vial preferably is closed, typically by a resealable rubber stopper. Many types of blood sample sampling devices have been developed, generally following the procedure of piercing the vial stopper to aspirate a portion or aliquot of the blood sample. The needle probe or cannula then is removed from the vial and the stopper reseals to maintain the remainder of the blood sample sealed in the vial.

For some operations, the blood sample is combined or mixed (prepared) with another fluid or reagent outside of the analyzer prior to being aspirated into the analyzer. If the vial is opened or handled for a transfer operation; the risk of exposure is greatly increased. The vials, typically made of glass can break, removing the stopper can result in aerosols, the contaminated stopper then must separately be disposed of and the risk of spillage also increases.

It therefore would be desirable to provide a method of transferring fluids between closed vials without exposing the operator to the fluids. Further, it would be desirable to transfer a precise desired volume of fluid between the vials.

SUMMARY OF THE INVENTION

The invention provides a method and apparatus for transferring fluids between closed vials. A transfer device includes a cylinder having a pair of opposing open tubes or tubular portions into which a pair of vials can be inserted to transfer fluid therebetween. The tubes are separated by a wall through which extends a vent needle and to a lesser distance, a fluid transfer needle. A first sample fluid containing vial, stopper first, is inserted into a first tube until seated onto an exposed end of the vent needle. This allows the first sample vial to be vented before it further is inserted onto the transfer needle. A second transfer vial, stopper first, then is inserted into the second tube until seated onto the opposite exposed end of the transfer needle. A negative pressure differential between the closed vials preferably can be utilized to transfer a desired fluid portion between the vials. The transfer device wall can include a vent chamber or reservoir into which the vent needle is connected to retain any expelled fluid or aerosol.

BRIEF DESCRIPTION OF THE DRAWINGS

FIG. 1 is an exploded perspective of one embodiment of a transfer device of the present invention;

FIG. 2 is a perspective view of a tube adapter which can be utilized with the transfer device of the present invention;

FIG. 3 is a side-plan view partially in section of the transfer device of the present invention with vials inserted therein;

FIG. 4 is a side view partially in section of a transfer wall and needle assembly of the transfer device of the present invention;

FIG. 5 is a top-plan view of a fixture which can be utilized with the transfer device of the present invention; and FIGS. 6–8 are side views of the transfer operation of the transfer device utilizing the fixture of FIG. 5.

DESCRIPTION OF THE PREFERRED EMBODIMENTS

Referring to FIGS. 1 and 3, a first embodiment of a closed vial transfer device of the present invention is designated generally by the reference numeral 10. As illustrated in FIGS. 1 and 3, the transfer device 10 has inserted therein a first vial or sample tube 12. The first vial 12 is inserted into a first tubular portion or tube 14 of the transfer device 10 through an open end 16. The tubular portion 14 includes a slot 18 formed therethrough and a tab 20 mounted in the slot 18.

The tab 20 preferably is formed or secured in a first position (FIG. 6) adjacent a first edge 22 of the slot 18. The first vial 12 is inserted against the tab 20, which forms a vent position and a vent needle 24 pierces a tube stopper 26 in the vial 18. The stopper 26 is conventionally formed and mounted in the open end of the first vial 12.

The vent needle 24 is mounted in a needle assembly 28 (FIGS. 1, 3, and 4). The needle assembly 28 is formed in a closed end 30 of a second tubular portion or tube 32. The end 30 can snap fit with a mating flange 34 on the tubular portion 14 to form a transfer housing or body. The tubular portions 14 and 32 can also be welded or adhered to one another or molded in one piece as desired.

The vent needle 24 opens into a vent chamber or reservoir 36 formed in the closed end 30 of the tubular portion 32. A second wall of the vent chamber 36 is formed by a hydrophobic member or pad 38. The first vial 12 is vented into the vent chamber 36, which will trap any fluid or aerosol which can be expelled from the first vial 12. The pad 38 is formed of a conventional high-surface tension material, which is selected to allow the air to pass through the pad 38, but prevents the fluid from passing therethrough. The fluid then is trapped in the reservoir 36.

The tab 20 preferably is formed as an integral snap tab with the edge 22, but could also be adhered to the edge 22. The tab 20 also could be rotatable from the vent position into the slot 18 for movement to the aspirating position. Once the first vial 12 is vented, the tab 20 is broken away or released from the edge 22 and the first vial 12 then can be moved to the aspirate position, as illustrated in FIGS. 1 and 3.

As the first vial 12 is moved into the aspirate position, a second transfer needle 40 pierces the stopper 26. The transfer needle 40 is mounted through the needle assembly 28 and is sealed from the chamber 36. The first vial 12 then is ready for a sample aliquot to be transferred to a second transfer vial 42. The transfer vial 42 has a stopper 44 and as the transfer vial 42 is inserted into the tubular portion 32, the stopper 44 is pierced by a free end 46 of the transfer needle 40.

The transfer vial 42 can include a reagent or can be empty, but in any case is maintained under a predetermined vacuum, which vacuum will draw the desired amount of the fluid in the first vial 12 into the transfer vial 42. The sample fluid is thus withdrawn simply from the first vial 12 into the transfer vial 42 without exposing the operator to the sample fluid or aerosols from the sample fluid. The tab 20 includes an opening 47 through which the needles 24 and 40 pass.

FIG. 2 illustrates the utilization of a smaller diameter sample vial 48, which can be a pediatric vial, when utilized with blood samples. An adapter sleeve 50 is utilized to properly insert the vial 48 into the center of the tubular portion 14 of the transfer device 10.

Referring now to FIGS. 5–8, a transfer operation is illustrated utilizing a fixture 52. The fixture 52 can include a plurality of sample vial wells 54 and the sample vial 12 is inserted into one of the wells 54. The second transfer vial 42 preferably is inserted in another well 56.

To transfer fluid, such as blood, between the vials 12 and 42, the vials 12 and 42 preferably first are inserted into the respective wells 54 and 56 of the fixture 52. The transfer device 10 then is mounted onto the vial 12 with the vial 12 being inserted into the first tubular portion 14. The vial 12 includes the stopper 26 into which the vent needle 24 first is inserted. The vial 12 is allowed to vent and the vent position is defined by a first vent position of the transfer device 10, as illustrated in FIG. 6.

The vent position is defined by the tab 20. As stated, the tab 20 can be a snap tab or can be a rotatable tab (not illustrated) mounted into the vent position of the slot 18. Once the first vial 12 is vented the tab 20 is snapped off or broken (not illustrated) or the tab 20 is rotated into the slot 18. Snapping the tab 20 or rotating it into the slot 18 allows the transfer device 10 to be inserted onto the first vial 12 a further distance which then inserts a first end of the transfer needle 40 through the stopper 26 into the first vial 12, as illustrated in FIG. 7.

The fluid in the first vial 12 then is ready to be transferred. The transfer device 10 then is inverted and is inserted over the second transfer vial 42. The second vial 42 also includes the stopper 44. The free end 46 of the transfer needle 40 is inserted through the stopper 44 and the fluid then preferably is transferred from the first vial 12 into the second vial 42 via a negative pressure differential between the two vials 12 and 42. The pressure is equalized, to allow the fluid transfer, by air passing back through the pad 38 and the transfer needle 40.

The second vial 42 then can be removed from the transfer device 10 and the fluid mixture then can be utilized/aspirated through the stopper 44 into an analyzer (not illustrated) without exposing the operator to the sample or reagent fluids. The first vial 12 can be removed from the transfer device 10 for further utilization or for disposal, also still in a sealed non-exposing mode, with the stopper 26 still intact.

Once the transfer operation is completed, the tab 20 can be moved back to the lip 22, which frees the stopper 26 from the transfer needle 40. The vial 12 then can be grasped and removed from the transfer device 10 with the stopper 26 secure in the vial 12. The tubular portion 14 preferably is sized such that the vial 12 cannot easily be twisted when it is seated on both the vent needle 24 and the transfer needle 40.

Although the transfer device 10 can be utilized in any transfer operation, it generally can be utilized to add a specific fluid aliquot from the sample vial 12 to a reagent contained in the transfer vial 42. The reagent can be any type of reagent which is to be combined with the sample aliquot. The reagent can be a chemical, a fluorescent labelled antibody or a monoclonal antibody bound to microspheres. The microspheres can be magnetic or non-magnetic and can be utilized for a variety of operations, such as disclosed in U.S. Pat. Nos. 5,223,398, 5,231,005 and 5,260,192.

One specific utilization of the transfer device 10 of the present invention is to obtain a lymphocyte subset determination, such as the CD4 or CD8 subsets, as described for example in U.S. application Ser. No. 08/303,924, entitled METHOD AND APPARATUS FOR SCREENING MICROSCOPIC CELLS UTILIZING LIGHT SCATTER TECHNIQUES, which is incorporated herein by reference. This application describes a procedure wherein, microspheres having a CD4 or CD8 monoclonal antibody bound thereto are first mixed with a whole blood sample, where the microspheres bind to the CD4 or CD8 positive cells, and then operated on in the instrument, such as a STKS analyzer sold by the assignee of the present invention, Coulter Corporation.

In this operation, the transfer device 10 can be utilized to transfer the desired aliquot of the whole blood sample from the vial 12 into the transfer vial 42. The transfer vial 42 has the reagent, CD4 or CD8 antibody bound microspheres, contained therein under vacuum. The vacuum is selected to draw a precise desired volume of the blood sample from the vial 12. The microspheres preferably are in a lyophilized form, but also can be in a liquid, if desired. Once the aliquot of blood is transferred into the vial 42, the vial 42 then is moved to a mixer, where the blood and reagent are mixed and then the vial 42 then can be utilized in the desired analyzer, all without exposing an operator to the sample fluid.

The transfer device 10 and one or more transfer vials 42 having a reagent under vacuum can be provided in a kit form for utilization in the above-referenced blood cell analysis operations. In one preferred embodiment, the transfer vial 42 can include about eighty (80) microliters of antibody bound microspheres in a liquid form or an equivalent lyophilized amount. The vacuum can be about 10–11 inches of mercury and the resultant transferred aliquot of whole blood will be on the order of eight hundred (800) microliters of blood, which then can be utilized for further blood cell analysis.

The kit (not illustrated) can include a transfer device 10 and one or more transfer vials 42, each counting a different reagent. One transfer device 10 can be utilized more than once, as long as the same sample is being transferred to the different transfer vials. If more than one sample is to be operated on, then a second set of one or more transfer vials and a transfer device will be included for the different samples.

The tubular portions 14 and 32 of the transfer device 10 and the vials 12 and 42 preferably are labeled, color coded, or otherwise identified for proper operation of the transfer device 10. The vials 12 and 42 also can be of different outer diameters, such that the primary or sample tube 12 only can be inserted into the tubular portion 14. The identification preferably is readily apparent for proper operation of the transfer device 10.

Many modifications and variations of the present invention are possible in light of the above teachings. The vials 12 and 42 can be conventional types of vials, formed of either glass or plastic. To ensure that the reagent and vacuum are contained in the transfer vial 42, the stopper 44 can be further secured by a screw-type cap, not illustrated. The vacuum is selected depending upon the volume of the sample fluid to be transferred and the size of the vials utilized. It is therefore, to be understood that within the scope of the appended claims, the invention may be practiced otherwise than as specifically described.

What is claimed is:

1. A method of transferring a blood sample between two closed vials comprising:

providing a first closed vial with at least with at least a blood sample therein;

piercing said first closed vial with at least a first vent needle to vent said first closed vial substantially to atmospheric pressure;

piercing said first closed vial with at least a first end of a substantially integral transfer needle spaced from said vent needle;

providing a second closed vial having an internal pressure less than atmospheric pressure and providing a negative pressure differential between said first and second closed vials; and piercing said second closed vial with at least a second end of said transfer needle to transfer a blood sample aliquot from said first closed vial to said second closed vial;

wherein said vent needle, said first end of said transfer needle and second end of said transfer needle are fully enclosed by a tubular member to eliminate human contact to an exposed needle or said blood.

2. The method as defined in claim 1 including providing a reservoir and venting said first closed vial into said reservoir.

3. The method as defined in claim 2 including providing said reservoir with at least a hydrophobic portion to trap fluid in said reservoir while allowing air to pass through the hydrophobic portion and out of said reservoir.

4. The method as defined in claim 1 including providing a needle assembly including a pair of open tubes and inserting said first closed vial into a first one of said tubes having said vent needle and a first end of said transfer needle therein and inserting said second closed vial into the second one of said tubes having a second end of said transfer needle therein.

5. The method as defined in claim 4 including providing a reservoir in said needle assembly and venting said first closed vial into said reservoir by inserting said vent needle into said first closed vial prior to inserting said transfer needle therein.

6. The method as defined in claim 5 including providing said reservoir with at least a hydrophobic portion to trap fluid in said reservoir while allowing air to pass through the hydrophobic portion and out of said reservoir.

7. The method as defined in claim 4 including identifying said tubes and said first and second closed vials to match only said first closed vial with said first tube and said second closed vial with said second tube.

8. The method as defined in claim 4 including providing said needle assembly with a physical stop to form a first vent position for said first closed vial and said first tube.

9. The method as defined in claim 8 including providing a reservoir in said needle assembly and venting said first closed vial into said reservoir, said reservoir including at least a hydrophobic portion to trap fluid in said reservoir while allowing air to pass through the hydrophobic portion and out of said reservoir, and identifying said tubes and said first and second closed vials to match only said first closed vial with said first tube and said second closed vial with said second tube.

10. The method as defined in claim 8 include moving said physical stop from said first vent position after venting said first closed vial to a second transfer position.

11. The method as defined in claim 10 including returning said physical stop to said first vent position to release said first closed vial after said fluid aliquot is transferred.

12. The method as defined in claim 10 including forming said physical stop as a tab in said first vent position.

13. The method as defined in claim 1 including forming a vacuum in said second closed vial to form said negative pressure differential between said first and second vials.

14. The method as defined in claim 13 including providing a reagent in said second closed vial.

15. The method as defined in claim 14 including forming a plurality of microspheres having a predetermined monoclonal antibody bound thereto as at least a portion of said reagent.

16. The method as defined in claim 15 including providing said reagent in a lyophilized form.

17. A transfer device for transferring a blood sample between a first and second closed vial having a pressure differential therebetween, the first closed vial containing at least a first blood sample therein comprising:

a housing including a first substantially tubular portion having a vent needle enclosed in said tubular portion and extending to a first position for piercing said first closed vial when inserted into said first tubular portion to said first position to vent said first closed vial, said first tubular portion further enclosing a substantially integral transfer needle having a first end extending to a second position removed from said first position for piecing said first closed vial after said vent needle in said second position, and said housing including a second tubular portion having a second end of said transfer needle fully enclosed therein and extending to a transfer position for piercing said second closed vial when inserted into said second tubular portion to said transfer position to transfer a portion of said blood sample from said first to said second closed vial utilizing said pressure differential wherein said vent needle, said first end of said transfer needle and second end of said transfer needle are fully enclosed by said tubular portion to eliminate human contact to an exposed needle or said blood.

18. The device as defined in claim 17 including a reservoir formed in said second tubular portion into which said first closed vial is vented.

19. The device as defined in claim 18 including said reservoir having hydrophobic means for trapping fluid in said reservoir while allowing air to pass through the hydrophobic means and out of said reservoir and out of said second tubular portion.

20. The device as defined in claim 17 including a needle assembly formed in said second tubular portion, said tubular portions formed as a pair of opposed open tubes and said first closed vial to be inserted into a first one of said tubes having said vent needle and a first end of said transfer needle therein and said second closed vial to be inserted into the second one of said tubes having a second end of said transfer needle therein.

21. The device as defined in claim 20 including a reservoir formed in said needle assembly and said first closed vial is vented into said reservoir by inserting said vent needle into said first closed vial prior to inserting said transfer needle therein.

22. The device as defined in claim 21 including said reservoir having hydrophobic means for trapping fluid in said reservoir while allowing air to pass through the hydrophobic means and out of said reservoir and out of said second tube.

23. The device as defined in claim 20 including means for identifying said tubes and said first and second closed vials to match only said first closed vial with said first tube and said second closed vial with said second tube.

24. The device as defined in claim 20 including said needle assembly having a physical stop to form a first vent position for said first closed vial and said first tube.

25. The device as defined in claim 24 including a reservoir in said needle assembly into which said first closed vial is vented, said reservoir including hydrophobic means for trapping fluid in said reservoir while allowing air to pass through the hydrophobic means and out of said reservoir, and means for identifying said tubes and said first and second closed vials to match only said first closed vial with said first tube and said second closed vial with said second tube.

26. The device as defined in claim 24 include said physical stop being movable from said first vent position after venting said first closed vial to a second transfer position.

27. The device as defined in claim 26 including said physical stop being movable to said first vent position to release said first closed vial after said fluid aliquot is transferred.

28. The device as defined in claim 26 including said physical stop is formed as a tab in said first vent position.

29. The device as defined in claim 17 including said second closed vial having a vacuum formed therein to form said negative pressure differential between said first and second vials.

30. The device as defined in claim 29 including a reagent in said second closed vial.

31. The device as defined in claim 30 including said reagent includes a plurality of microspheres having a predetermined monoclonal antibody bound thereto as at least a portion of said reagent.

32. The device as defined in claim 31 including said reagent being in a lyophilized form.

* * * * *